United States Patent
Yang et al.

(10) Patent No.: US 10,783,635 B2
(45) Date of Patent: Sep. 22, 2020

(54) METHOD AND SYSTEM FOR ROBUST IMAGE DETECTION FOR AUTOMATIC DETECTION OF SYMPTOMS

(71) Applicant: GRAFTY, INC., Sunnyvale, CA (US)

(72) Inventors: Allen Yang Yang, San Ramon, CA (US); Manish Mukherjee, Sunnyvale, CA (US)

(73) Assignee: GRAFTY, INC., Sunnyvale, CA (US)

( * ) Notice: Subject to any disclaimer, the term of this patent is extended or adjusted under 35 U.S.C. 154(b) by 14 days.

(21) Appl. No.: 16/353,900

(22) Filed: Mar. 14, 2019

(65) Prior Publication Data

US 2019/0295256 A1    Sep. 26, 2019

Related U.S. Application Data

(60) Provisional application No. 62/711,382, filed on Jul. 27, 2018, provisional application No. 62/645,586, filed on Mar. 20, 2018.

(51) Int. Cl.

| | |
|---|---|
| *G06T 7/00* | (2017.01) |
| *A61M 1/28* | (2006.01) |
| *A61J 1/10* | (2006.01) |
| *G06T 5/00* | (2006.01) |
| *G06T 3/40* | (2006.01) |
| *G06K 7/14* | (2006.01) |
| *G06K 7/10* | (2006.01) |
| *G06T 3/60* | (2006.01) |

(52) U.S. Cl.
CPC ............... *G06T 7/0014* (2013.01); *A61J 1/10* (2013.01); *A61M 1/28* (2013.01); *G06K 7/10722* (2013.01); *G06K 7/1413* (2013.01); *G06K 7/1417* (2013.01); *G06T 3/40* (2013.01); *G06T 3/60* (2013.01); *G06T 5/002* (2013.01); *A61M 2205/3306* (2013.01); *A61M 2205/6072* (2013.01); *G06T 2207/30092* (2013.01)

(58) Field of Classification Search
CPC ........... G06T 7/0014; A61J 1/10; A61M 1/28; G06K 7/10722
USPC ...................................... 235/462.01
See application file for complete search history.

(56) References Cited

U.S. PATENT DOCUMENTS

| | | | |
|---|---|---|---|
| 2009/0149776 A1 | 6/2009 | Adams | |
| 2013/0193211 A1 | 8/2013 | Baqai et al. | |
| 2015/0224243 A1* | 8/2015 | Elahi ...................... | G06Q 50/24 |
| | | | 604/29 |
| 2017/0319770 A1* | 11/2017 | Fitzgerald ........... | A61M 1/1656 |
| 2018/0236157 A1* | 8/2018 | Wolf ........................ | A61M 1/28 |

(Continued)

FOREIGN PATENT DOCUMENTS

WO    WO 2018/007013 A2    7/2018

OTHER PUBLICATIONS

WO, International Search Report & Written Opinion, Application No. PCT/IB2019/022329, dated Jul. 2, 2019.

(Continued)

*Primary Examiner* — Michael G Lee
*Assistant Examiner* — David Tardif
(74) *Attorney, Agent, or Firm* — Orrick, Herrington & Sutcliffe LLP

(57) ABSTRACT

A system and method for automatic detection of symptoms of peritonitis during peritoneal dialysis, such as using a mobile device with an image capturing system.

20 Claims, 8 Drawing Sheets

(56) References Cited

U.S. PATENT DOCUMENTS

2018/0250462 A1* 9/2018 Groder ............... A61M 1/1696

OTHER PUBLICATIONS

Baghaie, Ahmadreza, et al., "Sparse and Low Rank Decomposition Based Batch Image Alignment for Speckle Reduction of Retinal OCT Images", arXis:1411.4033v3 [cs.CV] Feb. 9, 2015.

* cited by examiner

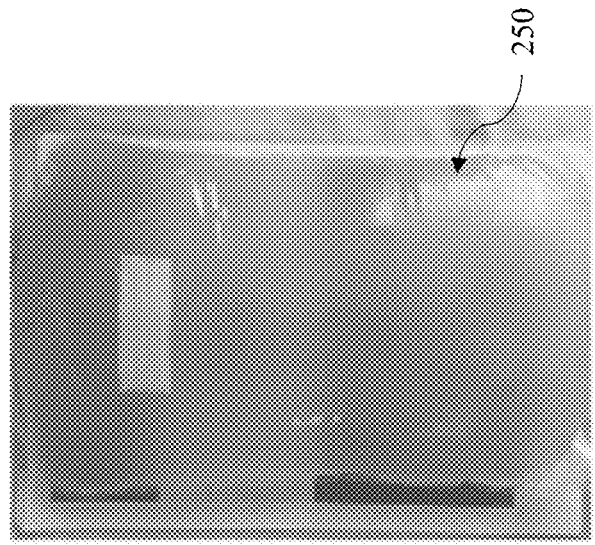
Fig. 5B
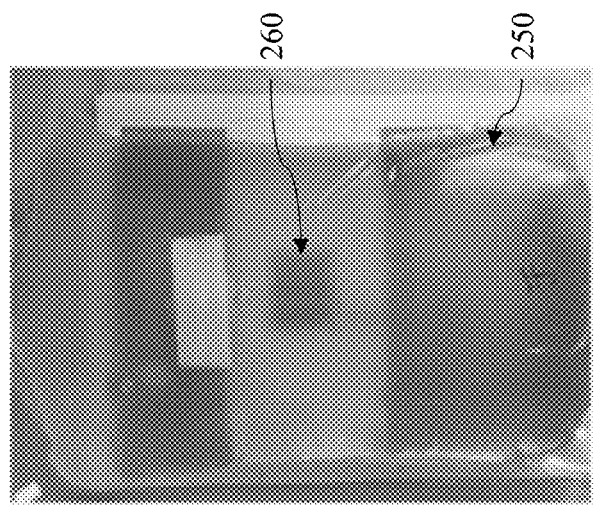
Fig. 5A
Fig. 5

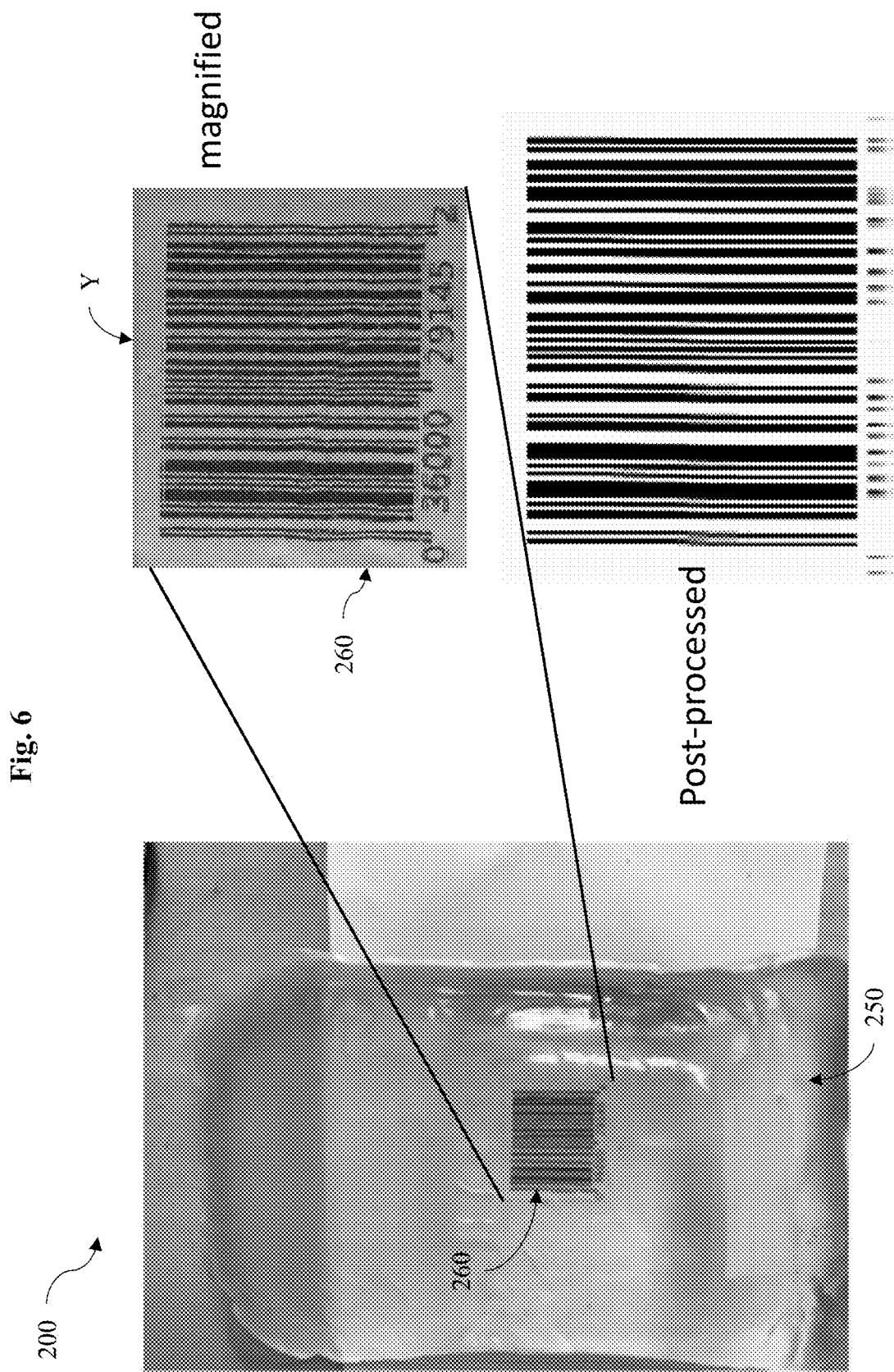

METHOD AND SYSTEM FOR ROBUST IMAGE DETECTION FOR AUTOMATIC DETECTION OF SYMPTOMS

RELATED APPLICATIONS

This application is a non-provisional of, and claims priority to, U.S. Provisional Application Ser. No. 62/645,586, filed on Mar. 20, 2018, and U.S. Provisional Application Ser. No. 62/711,382, filed on Jul. 27, 2018, the disclosures of the provisional applications are hereby incorporated by reference in their entireties and for all purposes.

FIELD

The present disclosure relates to systems and methods for image analysis and medical diagnostic testing using the same. More specifically, but not exclusively, the present disclosure relates to a system and method for robust image detection, such as for the automatic detection of symptoms of peritonitis during peritoneal dialysis.

BACKGROUND

Patients with severe chronic kidney disease can be treated with peritoneal dialysis (PD). A common complication of PD is peritonitis, which is a common cause that can force patients to temporarily, or permanently, discontinue PD. Late diagnose of peritonitis can further lead to death.

Furthermore, there are a number of complications that can occur during PD including, for example, the complications discussed in "Differential Diagnosis of Cloudy effluent in Peritoneal Dialysis," available at https://www.slideshare.net/ssuser79d8c1/differential-diagnosis-of-cloudy-effluent-in-peritoneal-dialysis, which slideshow is herein incorporated by reference in its entirety.

To detect early signs of complications during PD, one of the visual signals is known as "cloudy effluent" or "cloudy bag", which refers to the effluent fluid becoming cloudy after application of PD. FIG. 1 illustrates some examples of effluent fluid following various PD stages. As shown in FIG. 1, from right to left, a normal PD effluent before an episode of rhabdomyolysis is shown undergoing discoloration through various stages of peritonitis.

As certified by PD pharmaceutical companies, the conventional approach for monitoring effluent fluid in hospitals and during at-home treatment sessions is to train a patient to look over a clear window located on the side of the effluent bag. The window is specifically designed for human visual inspection (or manual inspection). For example, sufficiently cloudy effluent fluid prevents the patient from clearly identifying any text, printed paper, or other visual signal placed under the bag. Stated in another way, if the patient cannot visually determine a text pattern through the filled bag, this is an indication of a possible infection. In this situation, the patient is advised to contact their care giver immediately for further lab testing to confirm possible peritoneal infection.

However, manual inspection has several drawbacks. For example, manual inspection requires patients to be trained. Additionally, manual inspection requires patients to have both the mental and visual capability to perform the inspection strictly following the standard treatment procedure. Often times, patients simply forget about the inspection. As a further disadvantage, manual inspection means the care giver might miss the opportunity to receive and analyze critical patient health data on a daily basis.

In view of the foregoing, a need exists for an improved system for medical diagnostic testing in an effort to overcome the aforementioned obstacles and deficiencies of conventional peritonitis detection methods.

BRIEF DESCRIPTION OF THE DRAWINGS

FIG. 5A is an exemplary photograph illustrating another embodiment of the medical diagnostic testing system of FIG. 2 where there is an infection.

FIG. 5B is an exemplary photograph illustrating another embodiment of the medical diagnostic testing system of FIG. 2 where there is an infection.

FIG. 6 is an exemplary photograph illustrating one embodiment of a robust image detection for the medical diagnostic testing system of FIG. 2.

Figure 1:
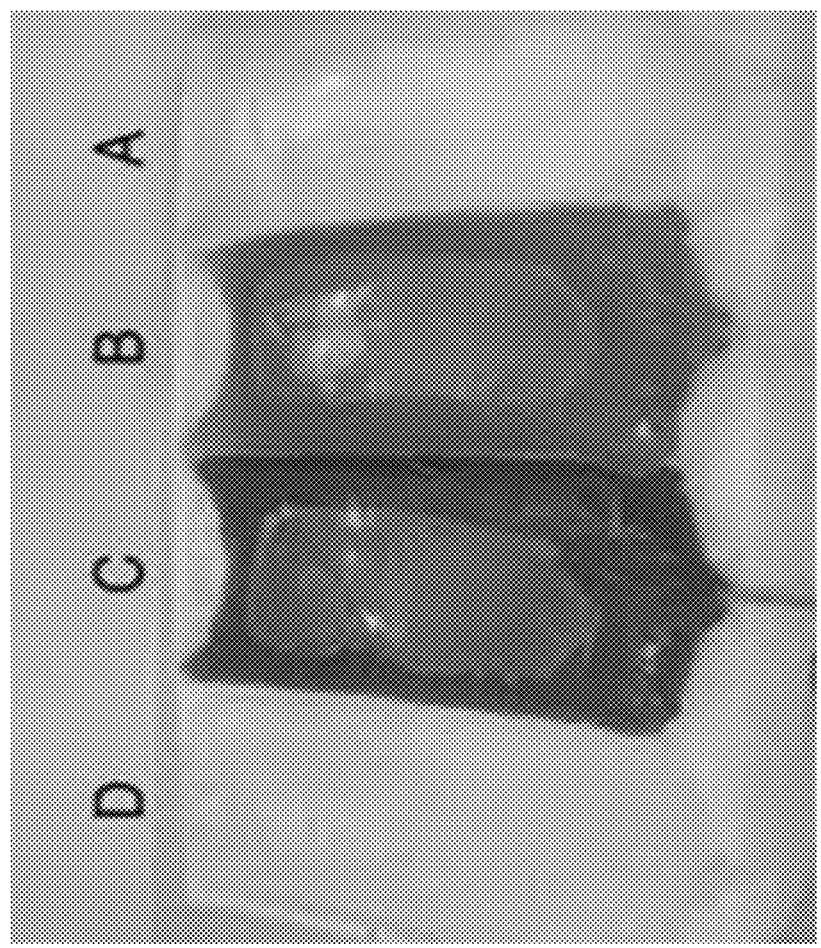
FIG. 1 is an exemplary photograph illustrating some embodiments of effluent fluid following peritoneal dialysis.

It should be noted that the figures are not drawn to scale and that elements of similar structures or functions are generally represented by like reference numerals for illustrative purposes throughout the figures. It also should be noted that the figures are only intended to facilitate the description of the preferred embodiments. The figures do not illustrate every aspect of the described embodiments and do not limit the scope of the present disclosure.

DETAILED DESCRIPTION

The present disclosure describes a number of methods and computerized systems for automatic detection of symptoms of peritonitis during peritoneal dialysis. Since currently-available medical systems and methods for PD treatment are deficient because they require self-reporting from patients and cannot provide automated medical inspection, a system for automatic detection of symptoms of peritonitis during peritoneal dialysis and reporting of the same can prove desirable and provide a basis for a wide range of medical applications, such as preventing erroneous manual inspection. This result can be achieved, according to one embodiment disclosed herein, by an image-based diagnostic system 200 as illustrated in FIG. 2.

Figure 2:
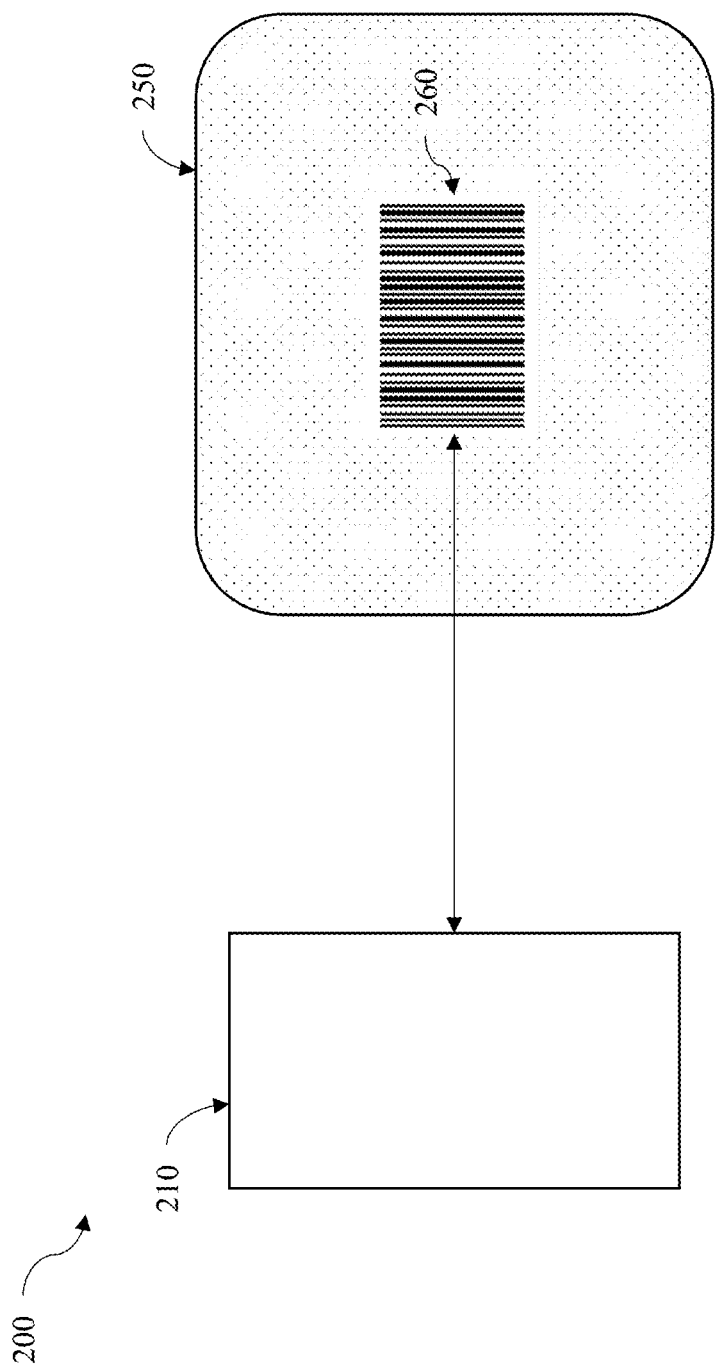
FIG. 2 is an exemplary block diagram illustrating one embodiment of a medical diagnostic testing system.
Figure 3A:
FIG. 3A is an exemplary photograph illustrating one embodiment of the medical diagnostic testing system of FIG. 2.
Figure 3B:
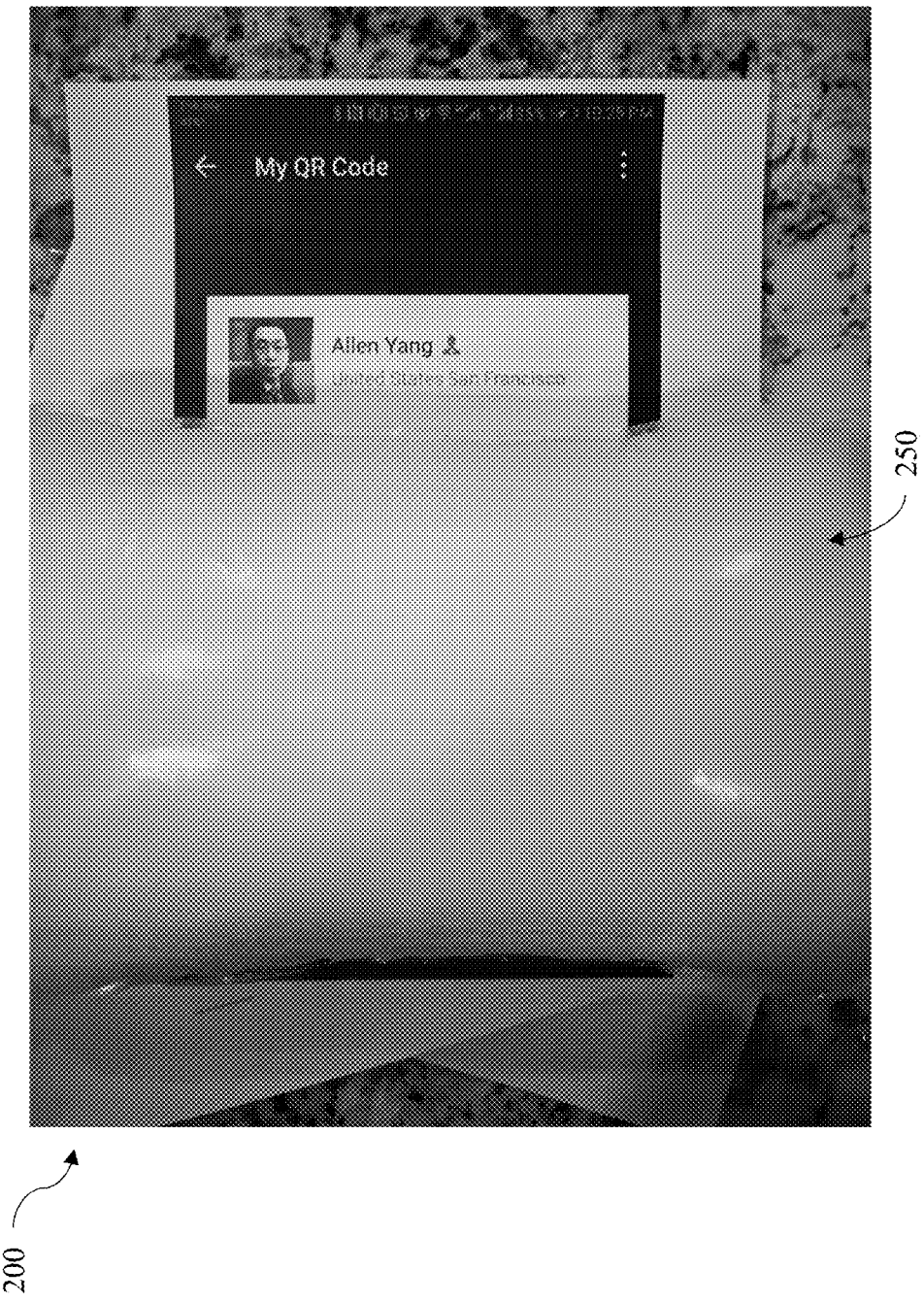
FIG. 3B is an exemplary photograph illustrating another embodiment of the medical diagnostic testing system of FIG. 2.
Figure 3C:
FIG. 3C is an exemplary photograph illustrating another embodiment of the medical diagnostic testing system of FIG. 2.

Turning to FIG. 2, a fully automatic PD infection detection system (e.g., the image-based diagnostic system 200) is shown. The image-based diagnostic system 200 includes an effluent bag 250. The effluent bag 250 collects the fluid removed from the body, for example, following PD. In a preferred embodiment, the effluent bag 250 defines a clear window to provide a transparent visual into the effluent bag 250. As shown in FIG. 2, the clear window of the effluent bag 250 exposes a visual signal 260. In a preferred embodiment, the visual signal 260 can be a barcode (such as shown in FIG. 2 and FIGS. 4-6) that is placed under the effluent bag 250. In another embodiment, the visual signal 260 can be a QR code (such as shown in FIGS. 3A-C). In use, the patient is asked to take a picture of the visual signal 260 through the clear-window. The picture will be supplied to an automatic barcode or QR-code reader program running on the computer.

In some embodiments, the patient takes a picture of the visual signal 260 with an image capturing device 210, such as a camera, that is communicatively coupled to a computer. In a preferred embodiment, the image capturing device 210 and computer is a smartphone having an onboard camera.

To differentiate possible positive and negative symptoms of peritonitis, the quality of the visual signal 260 as captured by the image capturing device 210 can be used. For example, if a method for QR-code reading can correctly decode the original QR-code because the fluid is sufficiently clear, the computer can determine that no infection exists. In some embodiments, if the method for QR-code reading can correctly generate an analog signal from the image of the QR-code, the QR-code can be sufficiently "decoded." Conversely, if the QR-code reader fails to identify the underlying QR-code pattern, the fluid is likely "cloudy" enough, thereby indicating a possible infection.

In the barcode example, if the barcode reading algorithm can correctly decode the original barcode, the computer can determine that no infection exists. In some embodiments, if the method for barcode reading can correctly generate an analog signal from the image of the barcode, the barcode can be sufficiently "decoded." Conversely, if the barcode reading algorithm fails to identify the underlying barcode pattern, the fluid is likely "cloudy" enough, thereby indicating a possible infection.

In some embodiments, the computer automatically uploads the recorded images of the effluent bag 250 and the automatic symptom detection provides results to a healthcare information system (not shown). For example, the result can be a flag or a probability for infection, such as described herein. Advantageously, the image-based diagnostic system 200 significantly improves the quality of care for at-home PD patients.

By way of example, FIGS. 3A-C illustrate various conditions of the fluid within the effluent bag 250 and the corresponding visibility of the visual signal 260. For example, FIG. 3A illustrates the effluent bag 250 having a sufficiently clear fluid, which suggests a negative example of peritoneal infection. In contrast, FIGS. 3B-C show effluent bags 250, each showing some positive symptom examples where a cloudy bag would fail the QR code reading.

Additionally and/or alternatively, the visual signal 260 placed under the clear window can be other bar codes, text, texture, or image patterns. In preferred embodiments, the visual signal 260 includes any symbol with a clarity that can be calculated by comparing the original pattern (which is known by the computer) and the captured image of the pattern.

In some embodiments, the visual signal 260 can be provided via any means described herein. For example, the visual signal 260 can be printed directly on the effluent bag 250 to further facilitate the procedure without the need of any additional media. Additionally, the visual signal 260 can also be displayed by digital screens disposed behind the effluent bag 250. In an even further embodiment, the visual signal 260 can be printed on any medium that can be placed underneath the effluent bag 250.

The image capturing device 210 can include any cameras, including RGB cameras, camera-enabled, and/or optical-based capturing device, such as, a portable camera, a digital camera, a hand-held game console, MP3 player, notebook computer, tablet PC, global positioning system, event data recorder, etc. The image capturing device 210 can include imaging sensors of other light spectrums, such as infrared cameras, black-and-white cameras, night-vision cameras, etc.

The recognition of the visual signal can also include QR-code or bar-code reader programs. Because the underlying pattern is known by the computer, a qualified detection method needs only to compare the pixel-value level difference between the ground truth and the captured patterns on the image. If the difference in a part of the pattern image is sufficiently large, it indicates the fluid in the bag is "cloudy" enough to alter the pattern shown under the imaging sensor.

In some embodiments, the image-based diagnostic system 200 can provide for a robust image detection of the visual signal 260. For example, existing barcode readers assume that the barcode pattern is directly exposed on the object surface. Namely, the distortion on the barcode image is minimal or inconsequential.

Figure 4:
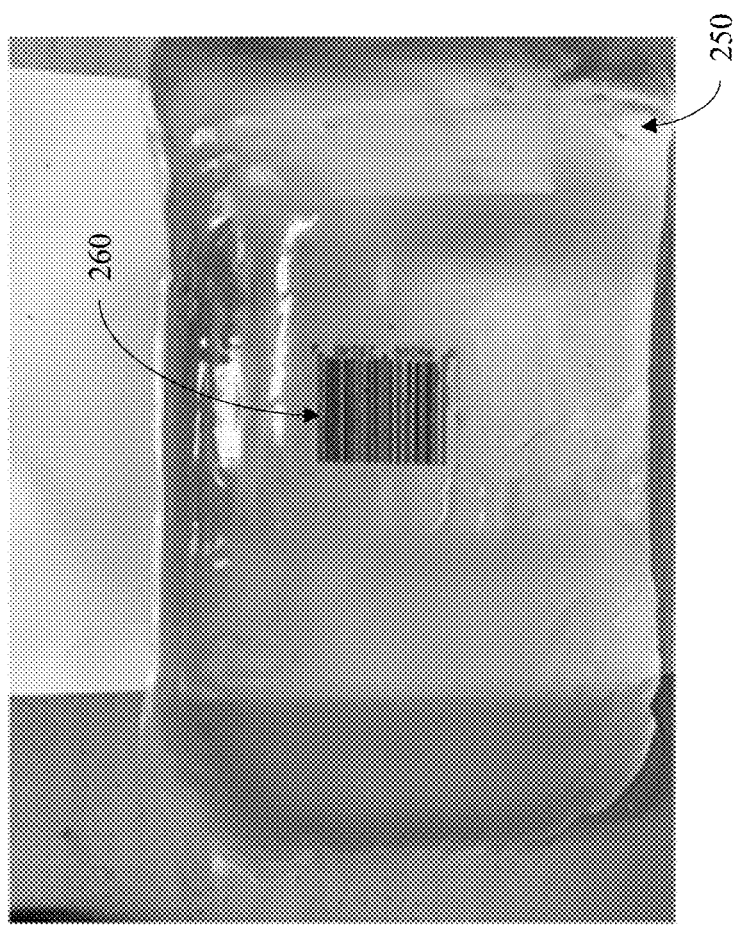
FIG. 4 is an exemplary photograph illustrating yet another embodiment of the medical diagnostic testing system of FIG. 2.

In some embodiments disclosed herein, however, the visual signal 260 is disposed under a media (such as under the effluent bag 250) that may significantly distort the quality of the image when being measured through the media, such as shown in FIG. 4. Often, this may not always suggest a symptom of PD as the original image quality can lead to some false negatives. Compare the situation where the cloudiness of the image is due to symptoms, such as shown in FIGS. 5A-B.

In the case of a bag of body fluid in some medical applications, the clarity of barcode images can be affected by bubbles in the fluid, watermark from plastic bag, and/or environmental/ambient lighting causing reflection, and/or the orientation of the barcode.

However, the barcode is robust to material media distortion because its image when treated as an image matrix shall be low-rank when no noise or correctable noise is present. Accordingly, in some embodiments, a numerical method to correct image noise by enforcing the resulting barcode image should be low-rank.

If low-rank property cannot be sufficiently enforced, then the media through which the image is acquired can be determined to be not clear. Then in its medical applications, one may reasonably infer that the fluid indicates the patient is infected.

Accordingly, a novel method for robust image detection is provided herein. First, a barcode region is cropped from the visual signal 260 that contains the barcode, called source image Y, such as shown in FIG. 6.

In some embodiments, the source image Y can be cleaned by converting to a black-and-white image, and hence increase the contract between black barcode pattern and white background. In such cases, the source image Y becomes a single-channel black-and-white image of dimensions w and h.

To correct image blemish, the source image Y can be decomposed into two images of the same dimension: Y=L+S, where L is a low-dimensional part, and S is a sparse noise part. Such optimization includes a low-rank matrix decomposition, such as a robust principal component analysis (RPCA) shown in Equation 1 below.

(* indicates matrix nuclear norm, subscript 1 indicates element-wise L-1 norm).

$$\text{minimize} \quad \|L\|_* + \lambda \|S\|_1 \quad \text{Equation 1}$$
$$\text{subject to} \quad L + S = Y.$$

Variations of RPCA can be considered for imposing different models of the sparse error term S. In one embodiment, the source image Y is distorted because its image is tilted, and hence its matrix rank is not minimized. In such cases, a branch and bound technique can be applied to quickly narrow down a range of tilt operator on the image.

Specifically, if the source image Y is assumed to be distorted by a rotation theta, then the source image Y can be rotated by a finite number of rotations (e.g., 60 degrees, 45 degrees, 30 degrees, 15 degrees, 0 degrees, −15 degrees, −30 degrees, −45 degrees, and −60 degrees).

After each rotation on Y, RPCA is implemented, and the rank of a resulting low-rank matrix L is measured. The lowest rank L indicates the branch and bound of the rotation. This process can be recursive. This process can be also applied to other transformational distortions, such as affine transform or homography transform, or other more complex nonlinear surface transform.

In another embodiment, the element-wise L-1 norm of S can be changed to other error norm functions. One of which is the column-wise L-1 norm, namely, it only enforces sparsity for the smallest number of nonzero columns, but within a nonzero column, it does not penalize the number of nonzero elements. This is particularly effective to denoise barcode images, the number of nonzero columns in the error term L should be as small as possible. However, many nonzero elements within a column can be used to correct image distortion.

Although described with reference to nuclear norm and L-1 norm matrix minimizations, one of ordinary skill in the art would appreciate that any RPCA/low-rank matrix decomposition, minimization, and/or approximation can be used. Stated in another way, any method for achieving robustness by enforcing a low-rank matrix property can be used as desired.

With the robust image detection disclosed herein, in some embodiments, the full barcode numbers can be successfully read correctly. This indicates a low-possibility of infection. The low possibility can also be measured by how much error is extracted in the S term.

Alternatively, if there is a complete failure to read, there is a high-possibility of infection. However, if a barcode is recovered by the numbers are only partially correct, the similarity of the barcode reading and the ground truth indicates the severity of the infection. For example, the automatic symptom detection can provide an event indicator for a possible infection. This may be a flag or a probability for infection. For example, if the barcode is completely clouded, there is a strong probability that the patient has an infection. Alternatively, if the barcode is readable, then an analysis of the sparse error term S can be used. For a larger sparse error, there may be more mass in the non-clean fluid. The barcode can also be compared between a ground truth and a read-out barcode. If the read-out barcode is the same as the ground truth printed, then the probability is lower for an infection. If there is a large distinction between the read-out barcode and the digits on the ground truth, then the probability for infection risk can be medium to high.

In a practical application, 114 Peritoneal Dialysis patients used the image-based diagnostic system 200, among which 74 were negative samples (i.e., no infection detected via lab work), and 40 were positive samples. The image-based diagnostic system 200 advantageously yielded a 95.2% True Positive and only a 1.4% False Negative when using visual signals for PD infection detection through non-contact analysis.

The disclosed embodiments are susceptible to various modifications and alternative forms, and specific examples thereof have been shown by way of example in the drawings and are herein described in detail. It should be understood, however, that the disclosed embodiments are not to be limited to the particular forms or methods disclosed, but to the contrary, the disclosed embodiments are to cover all modifications, equivalents, and alternatives.

What is claimed is:

1. A system for automatic detection of symptoms of peritonitis during peritoneal dialysis, comprising:
    an image capturing device in communication with a processor;
    an effluent bag for receiving effluent fluid during peritoneal dialysis, the bag having a clear window for visual inspection of the effluent fluid; and
    a visual signal disposed on a surface of the effluent bag for being inspected by the image capturing device through the effluent fluid, the visual signal being a computer-readable signal when no distortions are present and wherein the quality of the visual signal through the effluent fluid on a captured image of the image capturing device determines the presence of an infection.

2. The system of claim 1, wherein the visual signal is a quick response (QR) code.

3. The system of claim 1, wherein the visual signal is a barcode.

4. The system of claim 1, wherein the image capturing device is a mobile device.

5. The system of claim 1, wherein the processor corrects image noise for robust image detection of the visual signal.

6. A computer-based method for automatic detection of symptoms of peritonitis during peritoneal dialysis using an image capturing device in communication with a processor of the computer, the method comprising:
    capturing an image via the image capturing device of a visual signal disposed on an internal surface of an effluent bag, the effluent bag for receiving effluent fluid during peritoneal dialysis and having a clear window for visual inspection of the effluent fluid, the visual signal being a computer-readable signal when no distortions are present and being visible through the effluent fluid via the clear window; and
    determining a quality of the visual signal through the effluent fluid of the captured image via the processor, wherein the quality of the visual signal on the captured image indicates the presence of an infection.

7. The method of claim 6, wherein said determining comprises determining whether the processor can scan the visual signal of the captured image.

8. The method of claim 6, wherein said capturing the image of the visual signal comprises capturing the image of a quick response (QR) code.

9. The method of claim 6, wherein said capturing the image of the visual signal comprises capturing the image of a barcode.

10. The method of claim 6, further comprising correcting image noise of the captured image.

11. The method of claim 10, wherein said correcting the image noise comprises:
    cropping a visual signal region from the captured image to generate a source image, the cropped visual signal region being defined by an area of the captured image consisting of the visual signal;
    converting the source image to a black-and-white image;
    decomposing the converted source image into two images having the same dimensions, wherein a first image is a low-dimensional portion and a second image is a sparse noise error term portion; and optimizing the converted source image by minimizing a sum of a nuclear normal of the first image and an element-wise L-1 normal of the second image, wherein said determining is based on the quality of the visual signal through the effluent fluid of the corrected image.

12. The method of claim 11, wherein said optimizing comprises using a low-rank matrix decomposition.

13. The method of claim 11, wherein said optimizing comprises using a robust principal component analysis.

14. The method of claim 11, further comprising rotating the source image by a predetermined number of rotations, wherein said converting the source image comprises converting the rotated source image.

15. A computer-based method for automatic detection of symptoms of peritonitis during peritoneal dialysis using an image capturing device in communication with a processor of the computer, the method comprising:

capturing an image via the image capturing device of a visual signal disposed on an internal surface of an effluent bag, the effluent bag for receiving effluent fluid during peritoneal dialysis and having a clear window for visual inspection of the effluent fluid, the visual signal being a computer-readable signal when no distortions are present and being visible through the effluent fluid via the clear window;

correcting image noise of the captured image; and attempting to generate, via the processor, an analog signal from the visual signal of the captured image, wherein the attempt to generate the analog signal from the visual signal on the captured image indicates the presence of an infection.

16. The method of claim 15, wherein said capturing the image of the visual signal comprises capturing the image of a quick response (QR) code.

17. The method of claim 15, wherein said capturing the image of the visual signal comprises capturing the image of a barcode.

18. The method of claim 15, wherein said correcting the image noise comprises:

cropping a visual signal region from the captured image to generate a source image, the cropped visual signal region being defined by an area of the captured image consisting of the visual signal;

converting the source image to a black-and-white image;

decomposing the converted source image into two images having the same dimensions, wherein a first image is a low-dimensional portion and a second image is a sparse noise error term portion; and optimizing the converted source image by minimizing a sum of a nuclear normal of the first image and an element-wise L-1 normal of the second image, wherein said attempting to generate is based on the generated analog signal of the visual signal through the effluent fluid of the corrected image.

19. The method of claim 15, further comprising rotating the source image by a predetermined number of rotations, wherein said converting the source image comprises converting the rotated source image.

20. The method of claim 15, wherein said attempting to generate the analog signal comprises determining whether the processor can decode the visual signal of the captured image.

* * * * *